United States Patent [19]

Badger et al.

[11] Patent Number: 4,772,607

[45] Date of Patent: Sep. 20, 1988

[54] DIALKENYL DERIVATIVES OF XANTHINE, PHARMACEUTICAL COMPOSITIONS AND METHODS OF USE THEREFOR

[75] Inventors: Edward W. Badger, Dexter; Harriet W. Hamilton, Chelsea, both of Mich.

[73] Assignee: Warner-Lambert Company, Morris Plains, N.J.

[21] Appl. No.: 885,057

[22] Filed: Jul. 14, 1986

Related U.S. Application Data

[63] Continuation-in-part of Ser. No. 864,939, May 20, 1986, abandoned.

[51] Int. Cl.$^4$ .................. C07D 239/36; A61K 31/52
[52] U.S. Cl. ...................................... 514/263; 544/267; 544/273
[58] Field of Search .............. 544/277, 276; 540/267; 514/263, 265

[56] References Cited

U.S. PATENT DOCUMENTS

| | | | |
|---|---|---|---|
| 3,624,215 | 11/1971 | Skokie | 424/253 |
| 3,624,216 | 11/1971 | Skokie | 424/253 |
| 4,089,959 | 5/1978 | Diamond | 424/253 |
| 4,364,922 | 12/1981 | Berne et al. | 424/253 |
| 4,452,788 | 6/1984 | Bristol et al. | 424/253 |
| 4,469,698 | 9/1984 | Ohilippossian | 424/253 |
| 4,593,095 | 6/1986 | Snyder et al. | 544/267 |

FOREIGN PATENT DOCUMENTS

| | | |
|---|---|---|
| 0894946 | 6/1984 | Belgium . |
| 0003874 | 2/1983 | European Pat. Off. . |
| 149578 | 1/1984 | European Pat. Off. . |
| 0031722 | 10/1961 | German Democratic Rep. . |
| 2075505 | 11/1981 | United Kingdom . |

OTHER PUBLICATIONS

Schwabe, Pharmacol., vol. 330, pp. 212–221 (1985).
Jacobsen, J. Med. Chem., vol. 28, pp. 1334–1340 (1985).
Hamilton et al., J. Med. Chem., vol. 28, pp. 1071–1079, (1985).
Daly et al., J. Med. Chem., vol. 28, pp. 487–492 (1985).

*Primary Examiner*—Nicholas S. Rizzo
*Attorney, Agent, or Firm*—Joan Thierstein

[57] ABSTRACT

The present invention is various novel diallyl analogs of xanthine. Additionally, the invention is pharmaceutical compositions having as the active compound diallyl analogs of xanthines and methods of use therefor. Processes of preparation of diallyl analogs of xanthine are also the invention. The use of the analogs relates particularly to a desirable affinity at adenosine receptors, particularly the $A_1$ receptor. The analogs are adenosine receptor antagonists. The analogs, thus, for example provide activity for use as a CNS stimultant cognition activator, antifibrillatory agent, and bronchodilator.

8 Claims, No Drawings

DIALKENYL DERIVATIVES OF XANTHINE, PHARMACEUTICAL COMPOSITIONS AND METHODS OF USE THEREFOR

This is a continuation-in-part of U.S. application Ser. No. 864,939, filed May 20, 1986 now abn.

BACKGROUND OF THE INVENTION

The present invention is various novel dialkenyl analogs of xanthine. Additionally, the invention is pharmaceutical compositions having as the active compound dialkenyl analogs of xanthines and methods of use therefore. Processes of preparation of diallyl analogs of xanthine are also the invention.

The use of the analogs relates particularly to a desirable affinity at adenosine receptors, particularly the $A_1$ receptor. The analogs are adenosine receptor antagonists. The analogs, thus, for example provide activity for use as a CNS stimulant cognition activator, antifibrillatory agent, and bronchodilator.

Xanthines and particularly alkyl derivatives thereof, having adenosine receptor affinity are well-known for use to treat cardiovascular diseases, as bronchodilators, and/or as psycotropic agents and CNS stimulants as well as diuretics, to treat migraine, allergies, also antihistamines and the like. See, for example, U.S. Pat. Nos. 4,469,698; Ser. No. 467,894; 3,624,216; 3,624,215; 6,664,953 and 4,364,922. Additionally, E. German No. 31722 abstracted in Derwent Abstr. No. 64/14969; European Patent Appl. No. 149578 abstracted in Derwent Abstr. No. 85-179222/30; European Patent Application No. 0038784 and German Application No. 3406275 abstracted in Abstr. No. 84-165234/27 show alkyl xanthines having various other substituents.

The $A_1$ and $A_2$ adenosine receptor activity of various xanthines is discussed in *Pharmcol.* (1985) 330: 212–221; *J. Med. Chem.* (1985) 28: 1334–1340; *J. Med. Chem.* (1985) 28: 1071-9; and *J. Med. Chem.* (1985) 28: 487–92.

Substituted 8-phenylxanthines as adenosine receptor antagonists are shown in U.S. Pat. No. 4,452,788. However, the present 1–3 diallyl substituents are not previously described therein.

Belgian Pat. No. 898946 discloses diallyl analogs of xanthines having an aryl in the 8-position, which is not now in the present invention. Further British Pat. No. 2075505 and U.S. Pat. No. 4,089,959 discloses dialkenyl analogs of xanthine having hydrogen, methyl or ethyl in the 8-position. Again such analogs are not the present invention.

A diallyl analog of xanthine is disclosed in an abstract which was published in the April 1986 Proceedings of the Federation of American Society for Experimental Biology, Vol. 45, No. 4, Mar. 5, 1986. However, there is no disclosure for its preparation. Further, the diallyl analog of xanthine disclosed was disclosed as a penultimate intermediate in a process to prepare (8-cyclopentyl-1,3-dipropylxanthine). The disclosed diallyl analog is now found to be pharmacologically active.

Finally, additional species, i.e. particularly 8-(2-amino-4-chlorophenyl)-3,9-dihydro-1,3-bis(2-propenyl)-1H-purine-2,6-dione, N-[3-(dimethylamino)-propyl]-4-(2,3,6,7-tetrahydro-2,6-dioxo-1,3-2-propenyl-1H-purine-8-yl)benzensulfonamide, 8-(4-sulfonylphenyl)-3,9-dihydro-1,3-bis(2-propenyl)-1H-purine-2,6-dione, 8-methyl-3,9-dihydro-1,3-bis(2-propenyl)-1H-purine-2,6-dione are disclosed by H. W. Hamilton, et al, *J. Med. Chem.* (1985) 28: 1071 having $A_1$ and $A_2$ adenosine receptor binding activity. Several other substituents including one allyl are also among the disclosures to species of the Hamilton et al reference. The species named from the Hamilton et al reference as well as the more recently disclosed diallyl analog of xanthine were all prepared subsequent to the time of the present invention.

Thus, the present invention is novel dialkenyl analogs of xanthine, and further the invention is novel pharmaceutical compositions of the novel analogs. Further, the invention is methods of use for the novel pharmaceutical compositions herein.

SUMMARY OF THE INVENTION

Accordingly, the present invention relates to a compound of the formula I

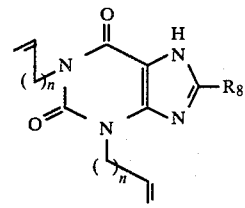

and the pharmaceutically acceptable salts thereof; wherein n is an integer of one, two, three or four;

$R_8$ is cyclic alkyl of from three through six carbons; aralkyl; or

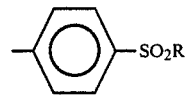

wherein R is (1) hydrogen; (2) straight or branched alkyl optionally substituted by amino, monoalkylamino, dialkylamino or hydroxyl, or cyclic alkyl of from one through six carbons; (3) $NR_1R_2$ wherein $R_1$ and $R_2$ are the same or different and are hydrogen; alkyl of from one through six carbon atoms; or when taken together form

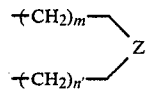

wherein m and n' are the same or different and are 1, 2, or 3 provided that the sum of m and n' is an integer of from three through six; and Z is a direct bond, O, $S(O)_R$ wherein k is 0, 1, or 2, or $NR_{10}$ wherein $R_{10}$ is hydrogen or alkyl of from one through six carbon atoms; or (4) $NH(CH_2)_{2-6}$—$NR_8R_9$ wherein $R_8$ and $R_9$ are the same or different and are hydrogen; or alkyl of from one through six carbon atoms; or when taken together form

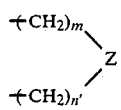

wherein m, n' and Z are as defined above.

Preferred compounds of the formula I are 8-cyclopentyl-3,7-dihydro-1,3-bis(2-propenyl)-1H-purine-2,6-dione;

N-[3-(dimethylamino)propyl]-4-(2,3,6,7-tetrahydro-2,6-dioxo-1,3-di-2-propenyl-1H-purine-8-yl)benzenesulfonamide, or the monohydrochloride salt thereof and 8-(2-amino-4-chlorophenyl)-3,9-dihydro-1,3-bis(2-propenyl)-1H-purine-2,6-dione.

The present invention also relates to a pharmaceutical composition for treating bronchoconstriction, depression, fibrillation or Alzheimer's disease comprising a bronchodilating, CNS stimulating, antifibrillatory or cognition activating amount of a compound of the formula (I)

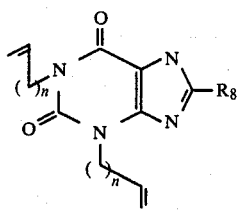

and the pharmaceutically acceptable salts thereof wherein n and $R_8$ are as defined above, together with a pharmaceutically acceptable carrier.

Finally, the present invention also relates to a method of treating bronchoconstriction, depression, fibrillation, or Alzheimer's disease in mammals, particularly humans suffering therefrom by administering to such humans the pharmaceutical composition defined above in unit dosage form.

The invention may also be a process of preparing the compound of formula I as defined above by a method as shown and defined hereinafter.

DETAILED DESCRIPTION OF THE INVENTION

"Cyclic alkyl of from three through six carbons" are cyclopropyl, cyclobutyl, cyclopentyl, or cyclohexyl.

"Ar" is phenyl unsubstituted or substituted by of from one through three substituents selected from the group comprising alkyl of one through six carbons; $OR_3$ wherein $R_3$ is hydrogen or alkyl, straight or branched, of from one through six carbons; halogen such as chloro, fluoro, or bromo; trifluoromethyl; nitro; amino; monoalkylamino; dialkylamino; $SR_3$ wherein $R_3$ is independently as defined above,

wherein $R_3$ is independently as defined above,

wherein $R_3$ is independently as defined above;

Aralkyl is an Ar as defined above; the Ar being attached through an alkyl, straight or branched, of from one through six carbons.

Monoalkylamino and dialkylamino are substituted amino wherein the alkyl is of from one through six carbons independently as defined above.

The compounds of formula I are useful both in the free base form, in the form of base salts where possible, and in the form of acid addition salts. The three forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as methanesulfonic acid, benzenesulfonic acid, p-toluenesulfonic acid, and the like, giving the hydrochloride, sulfate, methanesulfonate, benzenesulfonate, p-toluenesulfonate, and the like, respectively or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di-, or trihydroxyalkylamines such as mono-, di-, and triethanolamine; amino acids such as arginine, and lysine; guanidine; N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.* (1977) 66(1): 1–19.)

The acid addition salts of said basic compounds are prepared either by dissolving the free base of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution.

The compounds of the invention may contain an asymmetric carbon atom. Thus, the invention includes the individual stereoisomers, and the mixtures thereof. The individual isomers may be prepared or isolated by methods known in the art.

The processes for preparing the compounds of the present invention are shown in Scheme 1 and Scheme 2 and also are described, generally, as follows:

Scheme 1

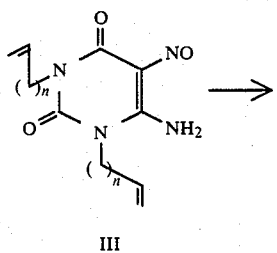

III

-continued
Scheme 1

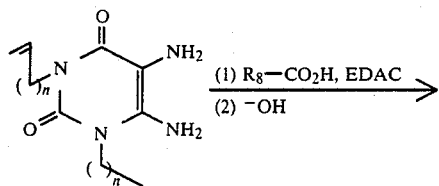

II

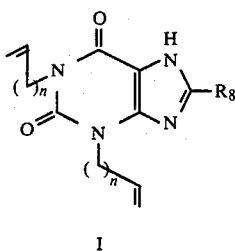

I

Generally, a 1,3-di(alkenyl)-5-nitroso-6-aminopyrimidinedione of the formula III wherein n is as defined above; is reduced with sodium dithionite in ammonium hydroxide, followed by isolation using conventional means. The resulting diamino uracil of the formula II wherein n is as defined above can then be coupled to an appropriate carboxylic acid of the formula $R_8CO_2H$ wherein $R_8$ is as defined above; utilizing a coupling reagent such as a carbodiimide (e.g. ethyl-dimethylaminopropylcarbodiimide, EDAC), or carbonyl diimidazole, and the resulting aminoamide uracil cyclized under basic conditions to afford products of structure I.

Scheme 2

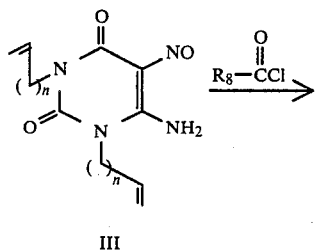

III

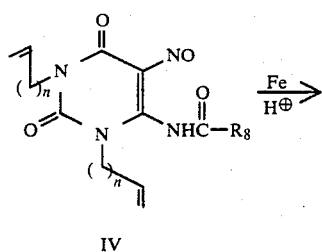

IV

-continued
Scheme 2

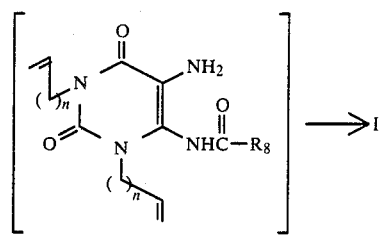

Alternatively, a 1,3-di(alkenyl)-5-nitroso-6-aminopyrimidinedione of the formula III wherein n is as defined above is reacted with an appropriate acid chloride of the formula $R_8C(O)Cl$ wherein $R_8$ is as defined above in an inert solvent, usually in the presence of a base such as triethylamine. The resulting amide-nitroso pyrimidinedione of the formula IV wherein n and $R_8$ are as defined above is then reduced using a metal such as iron in the presence of acid such as sulfuric, hydrochloric, or the like, which effects cyclization to the desired product I.

The starting material of each of Schemes 1 and 2 having the formula III as defined above is generally prepared by refluxing a reaction solution of (1) 1,3-di(alkenyl)urea of the formula X

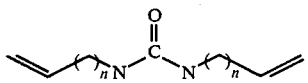

wherein n is as defined above;
(2) cyanoacetic acid and (3) acetic anhydride for from about one to three hours, then the reaction solution is reduced in volume and basified to a pH greater than 10 by addition of sodium hydroxide, first in an aqueous solution then by pellet. A suspension results to which is added about an equivalent of sodium nitrite followed by acetic acid to provide the desired product of formula III.

The products of each of the reactions described herein are isolated by conventional means such as extraction, distillation, chromatography, and the like.

The salts of compounds of formula I described above are prepared by reacting the appropriate base with a stoichiometric equivalent of the acid compounds of formula I, or of the appropriate acid with compounds of formula I having a base moiety.

The compounds of this invention may also exist in hydrated or solvated form.

The compounds of formula I have been found to have advantageous receptor affinities, particularly AI receptor affinities providing activity as bronchodilators, CNS stimulants, antifibrillators and/or cognition activators.

PHARMACOLOGICAL EVALUATION

Adenosine Receptor Binding—$A_1$ Receptor Affinity (RBA1)

Preparation of Membranes

Whole brain minus cerebellum and brainstem from male Long-Evans rats (150–200 g) is homogenized in 30 volumes of ice-cold 0.05M Tris-HCl buffer pH 7.7 using a Brinkman Polytron PT-10, (setting number 6 for 20 seconds) and centrifuged for ten minutes at 20,000×g (Sorvall RC-2), 4° C. The supernatant is discarded, and the pellet is resuspended and centrifuged as before. The pellet is resuspended in 20 ml Tris-HCl buffer containing two International Units/ml of adenosine deaminase (Sigma type III from calf intestinal mucosa), incubated at 37° C. for 30 minutes, then subsequently at 0° C. for ten minutes. The homogenate is again centrifuged, and the final pellet is resuspended in ice-cold 0.05M Tris-HCl buffer pH 7.7 to a concentration of 20 mg/ml original wet tissue weight and used immediately.

Assay Conditions

Tissue homogenate (10 mg/ml) is incubated in 0.05M Tris-HCl buffer pH 7.7 containing 1.0 nM [$^3$H]-N6-cyclohexyladenosine ([$^3$H]-CHA) with or without test agents in triplicate for one hour at 25° C. Incubation volume was 2 ml. Unbound [$^3$H]-CHA is separated by rapid filtration under reduced pressure through Whatman glass fiber (GF/B) filters. The filters are rinsed three times with 5 ml of ice-cold 0.05M Tris-HCl buffer pH 7.7. The radio-labeled ligand retained on the filter is measured by liquid scintillation spectrophotometry after shaking the filters for one hour or longer on a mechanical shaker in 10 ml of Beckman Ready-Solv HP scintillation cocktail.

Calculations

Nonspecific binding is defined as the binding which occurs in the presence of 1 mM theophylline. The concentration of test agent which inhibited 50% of the specific binding (IC$_{50}$) is determined by nonlinear computer curve fit. The Scatchard plot is calculated by linear regression of the line obtained by plotting the amount of radioligand bound (pmoles/gram of tissue) versus $$\left[ \frac{\text{bound radioligand}}{\text{free radioligand}} \right]$$

Since the amount of radioligand bound is a small fraction of the total amount added, free radioligand is defined as the concentration of (nM) of radioligand added to the incubation mixture. The Hill coefficient is calculated by linear regression of the line obtained by plotting the log of the bound radioligand vs the log of the $$\left[ \frac{\text{bound radioligand}}{B_{max} - \text{bound radioligand}} \right].$$

The maximal number of binding sites (B$_{max}$) is calculated from the Scatchard plot.

Adenosine Receptor Binding—A$_2$ Receptor Affinity (RBA2)

Tissue Preparation

Brains from 200–500 g mixed sex Sprague-Dawley rats are purchased from Pel-Freez (Rogers, Ark.). Fresh brains from male Long-Evans hooded rats (Blue Spruce Farms, Altamont, NY) give essentially identical results. Brains are thawed and then kept on ice while the striata are dissected out. Striata are disrupted in 10 vol of ice-cold 50 mM Tris·HCl (pH 7.7 at 25° C., pH 8.26 at 5° C.) (Tris) for 30 seconds in a Polytron PT-10 (Brinkman) at setting 5. The suspension is centrifuged at 50,000×g for ten minutes, the supernatant discarded, the pellet resuspended in 10 vol ice-cold Tris as above, recentrifuged, resuspended at 1 g/5 ml, and stored in plastic vials at −70° C. (stable for at least six months). When needed, tissue is thawed at room temperature, disrupted in a Polytron, and kept on ice until used.

Incubation Conditions

All incubations are for 60 minutes at 25° C. in 12×75 mm glass tubes containing 1 ml Tris with 5 mg original tissue weight of rat weight of rat striatal membranes, 4 nM [$^3$H]-N-ethyl adenosine-5′-carboxamide ([$^3$H]NECA), 50 nM N6-cyclopentyladenosine (to eliminate A$_1$ receptor binding), 10 mM MgCl$_2$, 0.1 units/ml of adenosine deaminase and 1% dimethylsulfoxide. N6-Cyclopentyladenosine is dissolved at 10 mM in 0.02N HCl and diluted in Tris. Stock solutions and dilutions of N6-cyclopentyladenosine can be stored at −20° C. for several months. Test compounds are dissolved at 10 mM in dimethylsulfoxide on the same day as the experiment, and diluted in dimethylsulfoxide to 100× the final incubation concentration. Control incubations receive an equal volume (10 μl) of dimethylsulfoxide; the resulting concentration of dimethylsulfoxide does not affect binding. [$^3$H]NECA is diluted to 40 nM in Tris. The membrane suspension (5 mg/0.79 ml) contained sufficient MgCl$_2$ and adenosine deaminase to give 10 mM and 0.1 units/ml, respectively, final concentration in the incubation. For test compounds with IC$_{50}$ values less than 1 μM, the order of additions is test compound (10 μl), N6-cyclopentyladenosine (100 μl), [$^3$H]NECA (100 μl), and membranes (0.79 ml). For test compounds with IC$_{50}$ values greater than 1 μM and limited water solubility, the order of additions (same volumes) is test compound, membranes, N6-cyclopentyladenosine, and [$^3$H]NECA. After all additions, the rack of tubes is vortexed, and the tubes are then incubated for 60 min at 25° C. in a shaking water bath. The rack of tubes is vortexed an additional time halfway through the incubation.

Incubations are terminated by filtration through 2.5 cm GF/B filters under reduced pressure. Each tube is filtered as follows: the contents of the tube are poured on the filter, 4 ml of ice-cold Tris are added to the tube and the contents poured onto the filter, and the filter is washed twice with 4 ml of ice-cold Tris. The filtration is complete in about twelve seconds. Filters are put in scintillation vials, 8 ml of Formula 947 scintillation fluid added, and the vials left overnight, shaken, and counted in a liquid scintillation counter at 40% efficiency.

Data Analysis

Nonspecific binding is defined as binding in the presence of 100 μM N6-cyclopentyladenosine, and specific binding is defined as total binding minus nonspecific binding. The IC$_{50}$ is calculated by weighted nonlinear least squares curve-fitting to the mass-action equation.

$$Y = T - S \cdot \frac{D}{D + K}$$

where
Y is cpm bound
T is cpm total binding without drug
S is cpm specific binding without drug
D is the concentration of drug and
K is the IC$_{50}$ of the drug Weighting factors are calculated under the assumption that the standard deviation was proportional to the predicted value of Y. Nonspecific binding is treated as a very large (infinite) concentration of drug in the computer analysis.

The IC$_{50}$ values (nM) for adenosine A$_1$ and A$_2$ receptor affinity are reported in the Table I.

TABLE I

| Example | Receptor Binding Data | |
|---|---|---|
| | RBA-1 (nM) | RBA-2 (nM) |
| 1 | 130 | — |
| 2 | 6960 | — |
| 3 | 260 | — |
| 4 | 9 | 3500 |

The above compounds may be compared to theophyline which binds the $A_1$ receptor at an $IC_{50}$ of 15000 nM and the $A_2$ receptor at an $IC_{50}$ of 32000 nM.

EVALUATION OF CENTRAL NERVOUS SYSTEM ACTIVITY

The purpose of this test is to identify drugs which antagonize the locomotor suppressant effects of $A_1$ and $A_2$ selective adenosine agonists in mice. Adenosine agonists produce inhibition of spontaneous exploratory activity in mice. This response has been demonstrated with the $A_1$ selective adenosine agonist CPA and the $A_2$ selective agonist CV-1808. The standard adenosine antagonist theophylline is active in this procedure by reversing the suppressant effects of both adenosine agonists. The procedure employs naive animals obviating the need for extensive training and precluding possible cumulative drug effects.

Method

Animals:

Male Swiss-Webster mice are used for this procedure. A minimum of 12 animals are used per dose including vehicle treated controls.

Drugs:

Compounds are dissolved or suspended in physiological saline containing Emulphor, 2-5%. Suspensions are ultrasonicated for 3 minutes. Drug doses are expressed as the active moiety and are administered intraperitoneally (IP) to mice in volumes of 10 ml/kg. CPA, $N^6$-cyclopentyladenosine, ($A_1$ agonist) and CV-1808, 2-anilinoadenosine, ($A_2$ agonist), are injected IP one hour before locomotor testing in respective doses of 2 and 8 mg/kg. The potential adenosine antagonist is injected 30 minutes before testing at the maximum dose which by itself has little or no effect on mouse locomotor activity.

Three control groups are utilized: a placebo control (vehicle treated mice used as an indication of base level locomotion); a reference control (a group of mice dosed with the antagonist alone to confirm the lack of locomotor response) and a positive control (a group of mice dosed with the agonist alone to demonstrate the inhibition of locomotion).

Procedure:

One hour after the agonist or vehicle injections and 30 minutes after the antagonist or vehicle injections, the mice are placed in darkened actophometers (3 mice/unit) and locomotor activity is monitored for 60 minutes. Activity counts are recorded automatically by a microcomputer.

Data Analysis:

Drug effects on locomotor activity are expressed as percent suppression relative to the vehicle treated (placebo) controls. The locomotor effect produced by the combination of agonist and antagonist (C) substrated from the locomotor suppressant effect of the agonist alone (B) is divided by the value for the agonist (B) and then multiplied by 100 to express the percent reversal. For example:

A. Theophylline, 10 mg/kg, alone produced locomotor stimulation (160% of placebo controls or −60% suppression).

B. CPA, 2 mg/kg, alone produced 94% suppression of locomotion.

C. Theophylline+CPA in combination produced stimulation (−42% locomotor suppression).

Then applying the formula: $(B-C)/B \times 100 = [94-(-60)]/94 \times 100 = 164\%$ reversal.

When theophylline was tested against CV-1808, 8 mg/kg, the data were as follows:

A. CV-1808 produced 83% suppression.

B. CV-1808+theophylline produced 22% suppression.

Then: $(83-22)/83 \times 100 = 73\%$ reversal.

The data (values for "B" and "C") are then analyzed in a paired t-test, if the values are significantly different ($p<0.05$) from each other then the dose effect is given a reversal rating of "A"; if the data are insignificant ($p>0.05$) then the dose effect is given a rating of "N". In the above examples, the effects of theophylline against both CPA and CV-1808 were rated "A" (active as an antagonist).

The above example contains an important variant to the criterion set forth in the methods: the dose of theophylline selected produced a significant effect on locomotion (160% relative to control). This dose was selected on the basis of previous results which indicated little or no effect of 10 mg/kg. It is not uncommon to see variation in the locomotor effect of doses which are bordering on profound pharmacological responses, e.g., 30 mg/kg of theophylline on previous testing had produced marked stimulation (200% of control) while 10 mg/kg had produced 118% of control. In light of this possible variation in the locomotor response to the antagonist it is deemed important that the effect of the antagonist alone is shown in order to facilitate understanding how a reversal effect can be more than 100%.

Results Example 4

| Dose | | Locomotor | |
|---|---|---|---|
| Agonist ($A_1$) CPA | Antagonist Ex 4 | Activity, % Suppression | % Reversal (B − C) ÷ B × 100. |
| 0.0 mg/kg | 10 mg/kg | A (−)20 | — |
| 2.0 | 0.0 | B 90 | — |
| 2.0 | 10 | C 16 | 82 |
| Agonist ($A_2$) CV-1810 | Ex 4 | | |
| 0.0 mg/kg | 10 mg/kg | A 18 | — |
| 8.0 | 0.0 | B 62 | — |
| 8.0 | 10 | C 57 | 8 |
| Reversal Rating | | | |
| | $A_1$-A | | |
| | $A_2$-N | | |

Accordingly, the present invention also includes a pharmaceutical composition for treating hypertension and a method for treating hypertension comprising administering to mammals, including humans, suffering therefrom either orally or parenterally the corresponding pharmaceutical composition. The composition contains a compound of the formula I or the formula IIa each as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 0.1 mg to 500 mg preferably to 1 to 100 mg according to the particular application and the potency of the active ingredient. The compositions can, if desired, also contain other compatible therapeutic agents.

In therapeutic use as described above, the mammalian dosage range for a 70 kg subject is from 0.1 to 150 mg/kg of body weight per day or preferably 1 to 100 mg/kg of body weight per day. The dosages, however, may be varied depending upon the requirements of the patient, the severity of the condition being treated, and the compound being employed.

Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Examples further illustrate the invention, but without, however, limiting it thereto.

PREPARATION I

6-Amino-5-nitroso-1,3-di-2-propenyl-2,4(1H,3H)-pyrimidinedione

A solution of 1,3-diallyl urea (69 g, 0.49 mol), cyanoacetic acid (42 g, 0.49 mol) and acetic anhydride (65 ml) is prepared and boiled under reflux for 3 hours. The resulting dark solution is distilled in vacuo to a small volume and combined with 250 ml of a 5% (w/v) aqueous sodium hydroxide solution, and the pH adjusted to greater than 10 via the addition of sodium hydroxide pellets, and allowed to stir for 30 minutes. The resulting suspension is filtered and the solids suspended in 250 ml water to which is added sodium nitrite (41.5 g, 0.6 mol) followed by acetic acid (60 ml) with rapid agitation. When this reaction mixture has cooled to 20° C., the purple solids are filtered, washed with water and a small amount of ethanol, and dried at 78° in vacuo to yield 29.3 g, mp 187°–188° C.

| Microanalysis | C | H | N | Ash |
|---|---|---|---|---|
| Calculated | 50.84 | 5.12 | 23.72 | 0.00 |
| Found | 50.60 | 5.21 | 23.33 | 0.37 |

EXAMPLE 1

8-(2-Amino-4-chlorophenyl)-3,9-dihydro-1,3-bis(2-propenyl)-1H-purine-2,6-dione A solution of 4-chloro-2-nitrobenzoyl chloride (0.212 mole) in tetrahydrofuran (200 ml) is prepared and added dropwise to a solution of 6-amino-5-nitroso-1,3-di-2-propenyl-2,4(1H,3H)-pyrimidinedione (25 g, 0.106 mol), triethylamine (31 ml, 0.22 mol), and tetrahydrofuran (500 ml) with vigorous stirring at 0°–10° C. When the addition is complete, the mixture is allowed to come to room temperature, filtered and the filtrate evaporated to dryness. The resulting gummy solid is dissolved in methanol (1500 ml), and to this solution is added 12N hydrochloric acid (265 ml, 3.18 mol) and powdered iron (88.8 g, 1.59 g). The resulting suspension is boiled under reflux for 4 hours with vigorous mechanical stirring, poured into ice water (2000 ml), and filtered. Solids thus collected are recrystallized from hot ethanol followed by recrystallization from hot 1:1 methanol:ethanol. Solids are dried overnight in vacuo at 78° to yield 1.38 g, mp 317–318.

| Microanalysis | C | H | N | Cl | Ash |
|---|---|---|---|---|---|
| Calculated | 57.07 | 4.51 | 19.57 | 9.91 | 0.00 |
| Found | 57.05 | 4.52 | 19.69 | 10.51 | 0.10 |

EXAMPLE 2

4-(2,3,6,7-Tetrahydro-2,6-dioxo-1,3-di-2-propenyl-1H-purine-8-yl)benzenesulfonic acid To a warmed solution of 6-amino-5-nitroso-1,3-di-2-propenyl-2,4(1H,3H)pyrimidinedione (2.32 g, 0.01 mol) in concentrated ammonium hydroxide (150 ml) is added a solution of sodium dithionite (5.3 g, 0.03 mol) in water (50 ml) dropwise with magnetic stirring. The resulting colored solution is stirred 18 hours and extracted three times with ethyl acetate (100 ml portions). The organics are combined, dried over anhydrous magnesium sulfate, filtered, and evaporated in vacuo to yield 0.85 g of a gummy solid which is dissolved in a warm solution of p-sulfobenzoic acid monopotassium salt (0.92 g, 0.004 mol) in water (25 ml). To the resulting solution is added EDAC [ethyl-dimethylaminopropylcarbodiimide] (0.75 g, 0.004 mol) and 0.1N hydrochloric acid (0.4 ml), and the resulting solution stirred for 1 hour. Solid potassium hydroxide is added in sufficient quantity to make the solution pH 13, and the resulting solution is boiled briefly, cooled, and treated with 12N hydrochloric acid to a pH of less than 1, resulting in a heavy precipitate of lusterous plates. This suspension is filtered and the solids thus obtained washed with 0.1N hydrochloric acid followed by diethyl ether, and finally dried in vacuo at 100° to yield 1.0 g, mp 340°–350° C. (dec).

| Microanalysis | C | H | N | S | Ash |
|---|---|---|---|---|---|
| Calculated | 52.57 | 4.15 | 14.43 | 8.25 | 0.00 |
| Found | 52.73 | 4.23 | 14.50 | 8.46 | 0.53 |

EXAMPLE 3

N-[3-(dimethylamino)propyl]-4-(2,3,6,7-tetrahydro-2,6-dioxo-1,3-di-2-propenyl-1H-purine-8-yl)benzenesulfonamide monohydrochloride To a solution of 4-(2,3,6,7)-tetrahydro-2,6-dioxo-1,3-di-2-propenyl-1H-purine-8-yl)benzenesulfonic acid (16 g, 0.04 mol) in dimethylformamide (250 ml) is added thionyl chloride (9 ml, 0.12 mol) with rapid mechanical stirring. The resulting solution is stirred for 18 hours with exclusion of moisture to yield a slightly cloudy solution. To this is added dimethylaminopropylamine (26.5 ml, 0.21 mol) in one portion with vigorous stirring. After stirring for 20 minutes, the resulting warm solution is concentrated to a viscous amber oil, which is dissolved in water (100 ml) and neutralized with dropwise addition of 12N hydrochloric acid, resulting in a precipitate. This material is collected by filtration, dried at 72° in vacuo for 16 hours, and recrystallized from ethanol to yield 11.54 g, mp 310°–330° C. (dec).

| Microanalysis | C | H | N | Cl | S |
|---|---|---|---|---|---|
| Calculated | 51.91 | 5.74 | 16.51 | 7.50 | 6.24 |
| Found | 51.46 | 5.87 | 16.14 | 7.42 | 6.39 |
| Karl-Fisher titration: Calc. 0.00%, found 0.21% | | | | | |

EXAMPLE 4

8-Cyclopentyl-3,7-dihydro-1,3-bis(2-propenyl)-1H-purine-2,6-dione

Prepared as in Example 1 substituting cyclopropanecarboxylic acid for p-sulfobenzoic acid monopotassium salt. Cyclopropanecarboxylic acid (3.2 g, 0.03 mol) yields 1.1 g of the ¼ hydrate product, after crystallization from ethanol. mp 178°–180° C.

| Microanalysis | C | H | N |
|---|---|---|---|
| Calculated | 63.04 | 6.78 | 18.38 |
| Found | 62.99 | 6.58 | 18.48 |

We claim:
1. A compound of the formula (I)

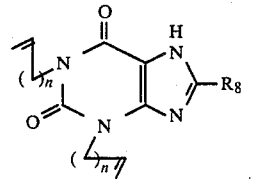

and the pharmaceutically acceptable salts thereof; wherein n is an integer of one, two, three, or four;

$R_8$ is cyclic alkyl of from three through six carbons; aralkyl wherein ar is phenyl unsubstituted or substituted by of from one through three substituents selected from the group comprising alkyl of one through six carbons; $OR_3$ wherein $R_3$ is hydrogen or alkyl, straight or branched, of from one through six carbons; halogen, trifluoromethyl; nitro; amino; monoalkylamino; dialkylamino; $SR_3$ wherein $R_3$ is independently as defined above,

wherein $R_3$ is independently as defined above,

wherein $R_3$ is independently as defined above and wherein ar is attached through an alkyl, straight or branched of from one through six carbons; or

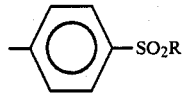

wherein R is (1) hydrogen; (2) straight, branched, optionally substituted by amino, monoalkylamino, dialkylamino or hydroxyl, or cyclic alkyl of from three through six carbons; (3) $NR_1R_2$ wherein $R_1$ and $R_2$ are the same or different and are hydrogen; alkyl of from one through six carbon atoms; or when taken together form

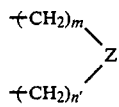

wherein m and n' are the same or different and are 1, 2, or 3 provided that the sum of m and n' is an integer of from three through six; and Z is a direct bond, O, $S(O)_R$ wherein k is 0, 1, or 2, or $NR_{10}$ wherein $R_{10}$ is hydrogen or alkyl of from one through six carbon atoms; or (4) $NH(CH_2)_{26}$—$NR_8R_9$ wherein $R_8$ and $R_9$ are the same or different and are hydrogen; or alkyl of from one through six carbon atoms; or when taken together form

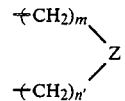

wherein m, n', and Z are as defined above.

2. A compound according to claim 1 wherein n is one.

3. A compound of claim 2 and being 4-(2,3,6,7-tetrahydro-2,6-dioxo-1,3-di-2-propenyl-1H-purine-8-yl)benzenesulfonic acid.

4. A compound of claim 2 and being N-[3-(dimethylamino)propyl]-4-(2,3,6,7-tetrahydro-2,6-dioxo-1,3-di-2-propenyl-1H-purine-8-yl)benzenesulfonamide.

5. The monohydrochloride salt of claim 4.

6. A compound of claim 2 and being 8-cyclopentyl-3,7-dihydro-1,3-bis(2-propenyl)-1H-purine-2,6-dione.

7. A pharmaceutical composition for use as a CNS stimulant comprising a CNS stimulant effective amount of a compound according to claim 1 together with a pharmaceutically acceptable carrier.

8. A method of treating depression in a mammal suffering therefrom comprising administering a compound of claim 1 in unit dosage form.

* * * * *

UNITED STATES PATENT AND TRADEMARK OFFICE
CERTIFICATE OF CORRECTION

PATENT NO. : 4,772,607

DATED : September 20, 1988

INVENTOR(S) : Edward W. Badger, et al

It is certified that error appears in the above—identified patent and that said Letters Patent is hereby corrected as shown below:

In column 16 line 2 change "$S(O)_R$" to --$S(O)_k$--.

In column 16 line 5 change "$NH(CH_2)_{26}$" to --$NH(CH_2)_{2-6}$--.

Signed and Sealed this

Fourteenth Day of February, 1989

Attest:

DONALD J. QUIGG

*Attesting Officer*    *Commissioner of Patents and Trademarks*